United States Patent [19]

Suzuki et al.

[11] Patent Number: 4,897,463
[45] Date of Patent: Jan. 30, 1990

[54] BIOLOGICALLY ACTIVE PEPTIDES WHICH INHIBIT TOXOPLASMA MULTIPLICATION

[75] Inventors: Naoyoshi Suzuki, Tokyo; Humio Osaki, Kobe, both of Japan

[73] Assignee: Nippon Mining Co., Ltd., Tokyo, Japan

[21] Appl. No.: 291,039

[22] Filed: Dec. 28, 1988

[30] Foreign Application Priority Data

Dec. 28, 1987 [JP] Japan .................. 62-330142

[51] Int. Cl.⁴ ................................ C07K 7/06
[52] U.S. Cl. .................... 530/329; 530/330
[58] Field of Search ............ 530/329, 330; 514/17

[56] References Cited

U.S. PATENT DOCUMENTS 4,482,543  11/1984  Suzuki et al. ............... 530/395
4,528,189   7/1985  Lederis et al. ............... 514/12

OTHER PUBLICATIONS

CA, vol. 108(5), 1988, p. 33938–Characterization of Multiple Forms of Maize Seedling Protein Kinases Reminiscent of Animal Casein Kinases S(Type 1), TS(Type 2), Dobrowolska et al.

Primary Examiner—Lester L. Lee
Attorney, Agent, or Firm—Sughrue, Mion, Zinn, Macpeak & Seas

[57] ABSTRACT

Biologically active peptides each having an activity to inhibit multiplication of toxoplasma and having a structure composed of amino acid sequence by the formula Gly-Glu-Glu-Glu-Glu-Glu; Glu-Glu-Glu-Glu-Glu; Asp-Asp-Asp-Asp-Asp; or Ala-Asp-Asp-Asp-Asp-Asp. These peptides are estimated to form active units or cores of Obioactin. The peptides may be applied in various dosage forms to human being and animals as immunoregulators against attack by toxoplasma, since they exhibit no specie specificity and have Toxo-GIF activities of 10 or more times on weight basis, and 40 or more time on molar basis, of that of the crude Obioactin.

4 Claims, 2 Drawing Sheets

BIOLOGICALLY ACTIVE PEPTIDES WHICH INHIBIT TOXOPLASMA MULTIPLICATION

BACKGROUND OF THE INVENTION

1. Field of the Invention

The present invention relates to biologically active peptides having activities to inhibit Toxoplasma multiplication.

*Toxoplasma gondii* is a sort of protozoa, which can proliferate in almost all cells of various mammals and birds in all over the world to cause various apriori and aquired diseases, such as cerebromeningitis, for human being and also to cause severe diseases of domestic animals. Unlike other microorganisms, the Toxoplasma organism evades the killing action of macrophage even after being taken by the macrophage of a normal host to reveal repeated fissiparous multiplication due to endogeneous budding.

On the other hand, the effect of inhibiting multiplication of the parasites in macrophages or the protozoacidal function of macrophages has been observed in a toxoplasma-hyperimmune animal, and it has been known that the serum of such an animal contains a mediator (generally referred to as "lymphokine") for inhibiting multiplication of toxoplasma in the normal cells of the animal. (See Reference No. 1. References cited herein will be listed collectively in the last portion of the specification.)

It has also been known that a lymphokine which inhibits multiplication of Toxoplasma in the homologous cells is existing in the supernatant of the culture medium obtained by cultivating spleen cells derived from a toxoplasma-hyperimmune animal in the presence of Toxoplasma lysate antigen (TLA). (See Reference Nos. 2 and 3.)

The lymphokine is a glycoprotein having a molecular weight of from 30,000 to 40,000, which is estimated to be a T-lymphocyte producing substance and referred to as Toxo-GIF (Toxoplasma Growth Inhibitory Factor). (See Reference Nos. 2 and 3.) The Toxo-GIF inhibits multiplication of Toxoplasma not only in the macrophage but also in other somatic cells. However, it only inhibits multiplication or protozoa in the cells of the same animal species, and cannot inhibit multiplication of protozoa in the cells of different animal species. (See Reference Nos. 3 and 4.)

Due to the species specificity described above, the Toxo-GIF cannot be used for the prevention or curing of toxoplasmosis of human being or various animals other than the host.

Under these circumstances, we have previously found and proposed a novel and epoch-making low molecular weight polypeptide which inhibits multiplication of Toxoplasma and is prepared by hydrolysis of serum of a toxoplasma-immune animal. (See Reference Nos. 5, 6 and 7.) The hydrolysate of the serum originated from a toxoplasma-immune animal is general referred to as "Obioactin". (See Reference No. 8.) This Obioactin is a polypeptide having a molecular weight of from 3,000 to 5,000 and inhibits multiplication of Toxoplasma not only in the homologous cells but also in heterologous cells. (See Reference No. 9.) Furthermore, the Obioactin has anti-microbial activities against various microorganisms, other protozoa, bacteria and viruses and also has anti-tumor activity, and hence it is applicable in immunoactive compositions. (See Reference Nos. 5, 6, 7 and 17.)

However, since the Obioactin is a refined product of a portion of a toxoplasma-immune serum, it is demanded to clarify the structure thereof, particularly the active core or unit, and to enable basic analysis of the mechanism of its function and mass production thereof by synthetic process.

OBJECT AND SUMMARY OF THE INVENTION

Accordingly, the primary object of this invention is to provide a novel biologically active peptide which is presumably estimated to be the active unit of Obioactin to enable to analyse the functional mechanism by Obioactin or to contribute mass production of Obioactin.

With the aforementioned object in view, the present invention relates to biologically active peptides each having an activity to inhibit Toxoplasma multiplication and having an amino acid sequence by the formula:

Gly—Glu—Glu—Glu—Glu—Glu;
Glu—Glu—Glu—Glu—Glu;
Asp—Asp—Asp—Asp—Asp; or
Ala—Asp—Asp—Asp—Asp—Asp.

More specifically, the present invention has been accomplished on the basis of the finding of the effect for inhibiting of multiplication of Toxoplasma during refining of the Obioactin, searching and estimating active units thereof and synthesis of the estimated peptides, and provides a new substance inhibiting multiplication of Toxoplasma and a novel immunoactive composition or immunoregulator.

It should be noted hereby that each of the left terminal amino acids is an N-terminal amino acid, and each of the right terminal amino acids is a C-terminal amino acid.

DESCRIPTION OF THE DRAWINGS

The present invention will be more clearly understood with reference to the following description of preferred embodiments along with the appended drawings in which.

DESCRIPTION OF PREFERRED EMBODIMENTS

Preparation of Obioactin

Obioactin was prepared through the Suzuki's Method (see Reference No. 8). In detail, tachyzoites of Toxoplasma RH strain ($1 \times 10^8$) was intravenously injected to a normal Holstein (6 to 8 months old), and at 5 weeks after the initial infection the same Toxoplasma RH strain ($1\times10^8$) was injected as a booster. At the second week from the boost, TLA (1 μg/kg body weight, prepared by the method of Igarashi et al. described in Reference No. 10) was intravenously injected, and the blood was extracted at 24 hours after TLA injection. The serum was obtained from the blood and subjected to latex agglutiation test to reveal that it had an antibody titer of above 1:3,200. Obioactin was prepared from the serum.

A protease (preferably pronase) was added in an amount of 0.1 g per 100 ml of serum, followed by incubation at 37° C. for 12 hours, and then 10 ml of a 10N aqueous sodium hydroxide solution was dropwisely added to 100 ml of serum to subject the serum to alkali hydrolysis at 100° C. for an hour. The reaction solution was then cooled to 4° C. and the pH value thereof was adjusted to 7.0±0.1 by the dropwise addition of a 10N hydrochloric acid.

The hydrolyzed serum was subjected to centrifugal separation at 10,000 rpm (10,700XG) to remove residues, and then subjected to gel filtration serially through Sephacryl S-200 (produced by Pharmacia Co.), Toyo-pearl HW-40 (produced by Toyo Soda Manufacturing co., Ltd.) and Sephadex G-15 (produced by Pharmacia Co.) to separate Toxo-GIF fraction. The separated Toxo-GIF fraction was lyophilized to obtain Obioactin.

Method of Measuring the Toxo-GIF Activity

The activity of Toxo-GIF was measured by a method developed by us. (See Reference Nos. 11 and 12.)

1 ml of a sterilized saline added with 0.2% of glycogen was injected into the peritoneal cavity of an adult BALB/c female mouse, and the peritoneal cavity was washed with cold Hanks' balanced salt solution (HBSS) to take up peritoneal exudate cells after the lapse of 5 days from the injection. After washing by centrifugal separation (250XG, 5 min.) for two times, the cells were allowed to suspend in 199 culture medium added with 10% of heat-inactivated calf serum (10%CS-Tc-199) in a ratio of $1\times10^6$ cells/ml. The cell suspension was fractionally poured, 1 ml each, into culture wells (Multi-dish-tray, FB-16-24-TC, Linblo chemical Co., U.S.A.) which were covered by a circular cover glass having a diameter of 15 mm, and cultured in a 5% $CO_2$-incubator. In order to remove contaminating erthrocytes and lymphocytes, the cultivation dish was rinsed gently with HBSS for three times at an interval of 2 hours and then cultivated for one night in a $CO_2$-incubator to make a macrophage monolayer on the cover glass.

After rinsing the monolayer again with a Tc-199 culture medium, the tachyzoites of Toxoplasma RH strain were added in a ratio $1\times10^5$ per $1\times10^6$ of macrophages so that the macrophages were infected thereby. The free Toxoplasma which did not penetrate into cells were removed by washing with HBSS after the lapse of an hour from the infection.

A culture medium containing each sample was added to the cover glass in an amount of 1 ml per $1\times10^6$ macrophages, followed by cultivation for 48 hours and then dyeing by May-Giemsa staining. The numbers of Toxoplasmas penetrating into the cells were counted. Within a certain visual field on the cover glass, 100 cells were checked to count the number of cells which contained no Toxoplasma, the number of cells which contained one to five Toxoplasmas and the number of cells which contained 6 or more Toxoplasmas, and the result was represented by percentage. Similar checking or counting operations were made within other four areas on the cover glass. The mean value and standard deviation of the data from the five areas were calculated to determine the percentage of cells containing Toxoplasmas.

As a different manner for the indication of activity, the Toxo-GIF activity was indicated by percentage which was calculated from the reduction rate (in percentage) of the cells containing Toxoplasma (Tp) caused by the addition of each sample material, the Toxo-GIF activity being calculated from the following equation of:

$$\text{Toxo-GIF Activity (\%)} = \left(1 - \frac{\text{Percentage of Tp-containing Cells with Added Sample}}{\text{Percentage of Tp-containing Cells with No Sample}}\right)\times 100$$

Each sample was prepared by dissolving a powder material in 3 ml of a 10% CS-Tc 199 culture medium and then filtering the solution through a membrane filter (Pore Size: 0.45 μm) so that the solution was filtered and sterilized.

The concentration of the sample material was controlled so that each fraction of Obioactin and refined Obioactin had a concentration of 5.0 mg/ml and that each of the synthesized peptides was contained in a ratio of 0.5 mg/ml.

The Toxo-GIF activities in the human cardiac muscle (Girardi Heart) cells and the celebral (Flow 3000) cells were measured by the following method.

Cells were suspended in the MEM-M culture medium (Nissui Seiyaku Co., Ltd.) added with a 10% heat-inactivated fetal calf serum (10%FCS-MEM) in a ratio of $1\times10^6$ cells/ml. One ml for each of the cell suspension was fractionally poured into culture wells (Multi-dish-tray, FB-16-24-TC, Linblo Chemical Corp., U.S.A.) covered by a circular cover glass having a diameter of 15 mm, and cultivated in a 5%-$CO_2$ incubator. After cultivating for one night in the 5%-$CO_2$ incubator, a monolayer of cells was formed over the cover glass.

After rinsing the monolayer with a MEM-M medium, the tachyzoites of Toxoplasma RH strain were added in a ratio of $1\times10^5$ per $1\times10^6$ of cell so that the cells were infected thereby. The free Toxoplasma which did not penetrate into cells were removed by washing with HBSS after the lapse of an hour from the infection.

A culture medium containing each sample was added to the cover glass in an amount of 1 ml per $1\times10^6$ macrophages, followed by cultivation for 48 hours and then dyeing with May-Giemsa staining. The numbers of Toxoplasmas penetrating into the cells were counted in the manner similar to the test for macrophage to determine the Toxo-GIF activity.

Refining of Obioactin (1) DEAE-5PW chromatography

Figure 1:
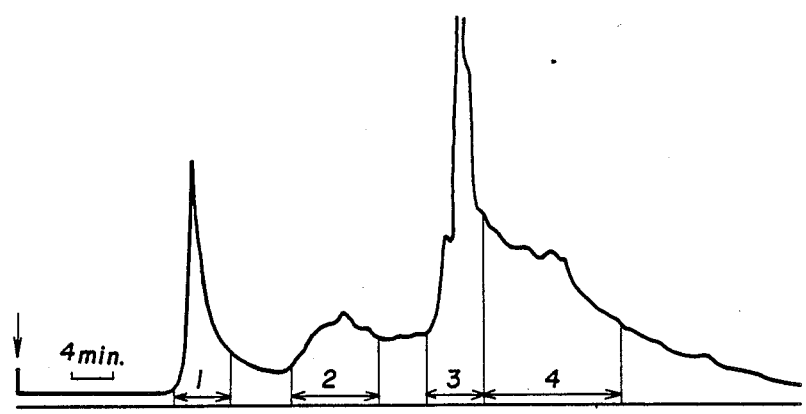
FIG. 1 is a chart showing the elution pattern from a DEAE-5PW column applied with Obioactin, the chromatography being effected under the following conditions of:
Column: DEAE-5PW
Inner Diameter=21.5 mm
Length=15 cm
Flow Rate: 3.0 ml/min.
Eluate:
0.02M CH₃COONH₄
0 to 1M NaCl
2 hrs., Linear Gradient
Wavelength: 280 nm
Sample:
Obioactin
100 mg/ml, 1 ml

The crude Obioactin prepared as described hereinbefore was fractionated by DEAE-5PW column (21.5 mm ID×15 cm) by NaCl gradient ion exchange chromatography with concentration gradient of NaCl of 0M to 1M in a basic solution of 0.02M ammonium acetate. The result is shown in FIG. 1. Each fraction was lyophilized, desalted by gel filtration through the Sephadex G-15 (Pharmacia Co.) and then lyophilized again. The powder sample of each fraction was dissolved in 10%CS-Tc 199 medium to prepare a solution containing 5 mg/ml of the sample, and the Toxo-GIF activity of each sample was measured by using mouse peritoneal macrophages.

As shown in Table 1, the Toxo-GIF activity was −38.2% for the first fraction, 10.8% for the second fraction, 23.1% for the third fraction and 16.1% for the fourth fraction. In view of the result, the third fraction was collected as the most active fraction, and refined by the following procedure.

TABLE 1

Activities for Inhibiting Multiplication of Toxoplasma by DEAE-5PW Fractions

| Sample | Percentage of Cells Containing Toxoplasma (%) | | | Toxo-GIF Activity (%) | Cytotoxicity |
| --- | --- | --- | --- | --- | --- |
| | 0 Tp | 1 to 5 Tp | ≧6 Tp/cell | | |
| Control (Tc-199) | 62.8 ± 7.5 | 22.6 ± 4.9 | 14.6 ± 3.9 | — | — |
| Fr. 1 | 48.6 ± 9.3 | 29.0 ± 3.8 | 22.4 ± 8.8 | −38.2 | — |
| Fr. 2 | 66.8 ± 15.7 | 17.8 ± 8.6 | 15.4 ± 8.8 | 10.8 | — |
| Fr. 3 | 71.4 ± 11.4 | 17.8 ± 4.8 | 10.8 ± 7.4 | 23.1 | — |
| Fr. 4 | 68.8 ± 10.8 | 17.4 ± 5.9 | 13.6 ± 5.6 | 16.1 | — |

(means ± S.D.)

(2) ODS-120T Reverse Phase Chromatography

Figure 2:
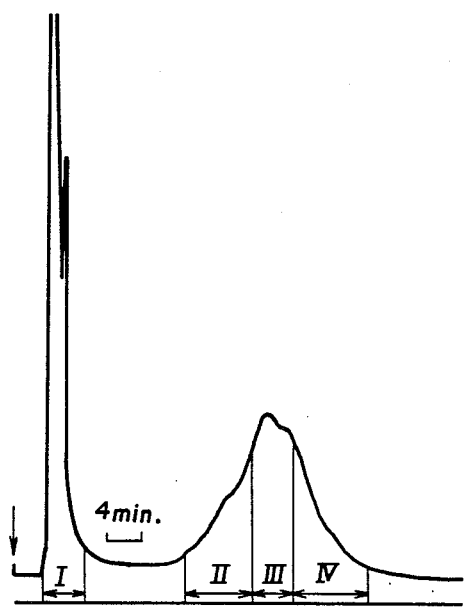
FIG. 2 is a chart showing the elution pattern from a ODS-120T column applied with a third fraction fractionated by DEAE-5PW column, the chromatography being effected under the following conditions of:
Column: ODS-120T
Flow Rate: 1.0 ml/min.
Eluate:
Initial Stage
Acetonitrile (10%)+0.1% TFA (90%)
Final Stage Acetonitrile (100%)
60 min., Linear Gradient
Wavelength: 230 nm
Sample: Third Fraction of DEAE-5PW

Using the ODS-120T column (Toyo Soda Manufacturing Co., Ltd.), the third fraction was subjected to reverse phase chromatography with the concentration gradient of 10% to 100% of acetonitrile in 0.1% trifluoroacetic acid solution. The result is shown in FIG. 2. Each fraction was concentrated under reduced pressure, and then lyophilized. The thus obtained powder of each fraction was subjected to test for Toxo-GIF activity.

As shown in Table 2, the Toxo-GIF activity was 97.6% for Fraction I, 96.8% for Fration II, 97.2% for Fraction III and 99.2% for Fraction IV. In view of the result, the most active fraction was the Fraction IV.

ANALYSES OF AMINO ACID COMPOSITION AND AMINO ACID SEQUENCE

The refined Obioactin fraction (ODS-120T Fraction IV) was put into a tube with 0.2 ml of a constant boiling point hydrochloric acid solution containing 0.1% of thioglycol and the tube was sealed. The content in the tube was heated to 110° C. for 24 hours to hydrolyse the Obioactin fraction, and the amino acid composition was analysed through the OPA method (see Reference Nos. 13 and 14) using the Hitachi Model 835 Amino Acid Analyser. The amino acid composition of ODS-120T Fraction IV was Asx (total of Asn+Asp) 30%, Glx (total of Glu+Gln) 43%, Gly 7%, Ala 6% and Cys 5%. Likewise, predominant amino acids of the other highly active fractions of ODS-120T were Asx, Glx, Gly and Ala, and Val. Pro and Try were also detected as minor components.

The amino acid sequence was analysed generally in accordance with the Edman degradation method using a Protein Sequencer produced by Biosearch 9600 (U.S.A.) The collected Edman cycles were converted to derivatives of 3-phenyl-2-thiohydantoin (PHT), and respective PTH-amino acids were identified by reverse phase high pressure liquid chromatography.

As shown in the following Table 3, the amino acids found from the N-terminal of the fraction IV of ODS-120T included glutamic acid (Glu), aspartic acid (Asp), glycine (Gly) and alanine (Ala) as the major constituents at the first cycle (first residue), and additionally valine (Val), proline (Pro) and tyrosine (Tyr) as the minor constituents. Glue and Asp were found as the major constituents of the second cycle which also contained Ala, Val and Pro. Glu and Asp were the major constituents of the third to seventh cycles. From the results described above, it was anticipated at high possibility that the refined Obioactin is a mixture composed of at least four components, which have Glu, Asp, Gly and Ala at N-terminal of each component, and second cycle et seq. is poly-Glu or poly-Asp.

TABLE 2

Activities for Inhibiting Multiplication of Toxoplasma by ODS-120T Fractions

| Sample | Percentage of Cells Containing Toxoplasma (%) | | | Toxo-GIF Activity (%) | Cytotoxicity |
| --- | --- | --- | --- | --- | --- |
| | 0 Tp | 1 to 5 Tp | ≧6 Tp/cell | | |
| Control (Tc-199) | 49.8 ± 16.3 | 26.8 ± 7.1 | 23.4 ± 9.3 | — | — |
| Fr. I | 98.8 ± 1.1 | 1.2 ± 1.1 | 0 | 97.6 | — |
| Fr. II | 98.4 ± 1.5 | 1.6 ± 1.5 | 0 | 96.8 | — |
| Fr. III | 98.6 ± 2.1 | 1.2 ± 1.6 | 0 | 97.2 | — |
| Fr. IV | 99.6 ± 0.5 | 0.4 ± 0.5 | 0 | 99.2 | — |

(means ± S.D.)

Similar analyses were performed with regard to the other fractions of ODS-120T reverse phase chromatography to reveal substantially same results. Every fraction of the ODS-120T reverse phase chromatography had substantially equivalent activities, and they could not be further refined by re-chromatography. It is estimated that such results are obtained due to the fact that the refined Obioactin is a mixture of peptides resembling with each other and having heterologous N-terminals. Although it has not been explicated why low molecular weight oligopeptides can be separated from the crude Obioactin having a molecular weight of 3,000 to 5,000, it is estimated that the units (active cores) of natural lymphokines are oligopeptides of low molecular weight, 10 to 20 units of such oligopeptides being bonded or associated with each other by weak bonds to form a high molecular weight aggregate which is dissociated to various fractions composed of several units and having different molecular weights during the refining operation. This is one of the causes which make it difficult to refine the Obioactin.

Anyway, it has been estimated by us from the aforementioned results that the active fractions of Obioactin has an N-terminal composed of Glu, Asp, Gly or Ala and 4 to 5 molecules of Glu or Asp are combined with the N-terminal.

Synthesis of Peptides and Toxo-GIF Activities Thereof

The following oligopeptides, which were estimated to be the smallest constituting units of Obioactin in view of the results of analysis of amino acids, were synthesized. The syntheses were carried out generally following to the known processes (see Reference Nos. 15 and 16).

Glu-Glu-Glu-Glu-Glu
  (penta-Glutaminate; pG)
Gly-Glu-Glu-Glu-Glu-Glu
  (Glycyl-penta-Glutaminate; GpG)
Ala-Glu-Glu-Glu-Glu-Glu
  (Alanil-penta-Glutaminate; ApG)
Asp-Asp-Asp-Asp-Asp
  (penta-Asparaginate; pA)
Gly-Asp-Asp-Asp-Asp-Asp
  (Glycyl-penta-Asparaginate; GpA)
Ala-Asp-Asp-Asp-Asp-Asp
  (Alanil-penta-Asparaginate; ApA)

Each of the synthesized peptides was dissolved in a culture medium (10%CS-Tc-199) in an amount of 0.5 mg/ml, and the Toxo-GIF activity thereof was measured while using mouse peritoneal macrophages. The results are shown in Table 4.

TABLE 4

Activity for Inhibiting Multiplication of Toxoplasma by Synthesized Peptide

| Sample (0.5 mg/ml) | Percentage of Cells Containing Toxoplasma (%) 0 Tp | 1 to 5 Tp | ≧6 Tp/cell | Toxo-GIF Activity (%) | Cytotoxicity |
|---|---|---|---|---|---|
| 10% CS—Tc-199 (Control) | 83.6 ± 3.6 | 7.6 ± 1.8 | 8.8 ± 3.5 | — | — |
| Glu—Glu—Glu—Glu—Glu | 89.4 ± 8.5 | 5.2 ± 4.9 | 5.4 ± 3.9 | 35.4 | — |
| Gly—Glu—Glu—Glu—Glu—Glu | 96.6 ± 3.4 | 2.6 ± 2.6 | 0.8 ± 0.8 | 79.3 | — |
| Ala—Glu—Glu—Glu—Glu—Glu | 76.0 ± 20.5 | 10.8 ± 7.6 | 13.0 ± 12.9 | −46.3 | — |
| Asp—Asp—Asp—Asp—Asp | 90.0 ± 8.5 | 3.8 ± 2.4 | 6.2 ± 6.4 | 39.0 | — |
| Gly—Asp—Asp—Asp—Asp—Asp | 83.2 ± 7.5 | 9.8 ± 4.6 | 7.0 ± 3.7 | −2.4 | — |
| Ala—Asp—Asp—Asp—Asp—Asp | 90.0 ± 6.0 | 5.8 ± 3.1 | 4.2 ± 3.3 | 39.0 | — |

(means ± S.D.)

As shown in Table 4, Toxo-GIF activities of respective peptides were 35.4% for pG, 79.3% for GpG, −46.3% for ApG, 39.9% for pA, −2.4% for GpA and 39.3% for ApA. All of the peptides did not exhibit cytotoxicity at that concentration (0.5 mg/ml).

In view of the results described above, it is estimated that GpG which has the highest activity is the active unit of Obioactin. GpG (glycyl-penta glutaminate) has a molecular weight of about 720. Likewise, pG, ApA and pA exhibit Toxo-GIF activities, and any of these synthesized peptides are expected to be used as chemicals having effect of inhibiting multiplication of Toxoplasma and promoting immunoreglation.

Figure 3:
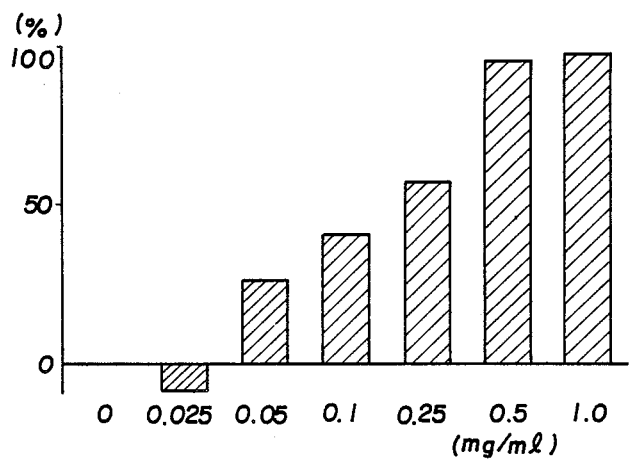
FIG. 3 is a histogram showing the dose response of glycyl-penta-glutaminate on Toxo-GIF activity.

The dose dependency of the activity of GpG having the highest activity was examined. As shown in the following Table 5 and FIG. 3, it showed Toxo-GIF activity at a concentration of above 0.05 mg/ml and the activity was saturated at a concentration of 0.5 mg/ml. At the concentration of 1.0 mg/ml, an image indicating shrinkage and exfoliation of the cells were found to reveal damages morphologically.

The Toxo-GIF activity of crude Obioactin becomes appreciable at a concentration of generally about 5 mg/ml, whereas sufficient Toxo-GIF activity of GpG is detected at a concentration of 0.25 mg/ml. In view of the above, it has been estimated that the activity of GpG is 10 to 20 times as high as that of crude Obioactin on weight basis, and 40 to 140 times as high as that of crude Obioactin on mole basis.

TABLE 3

Amino Acid Sequence in Refined Obioactin (ODS-120T Fr. IV)

| Amino Acid No. | Glu | Asp | Gly | Ala | Val | Pro | Tyr | Leu | Ile | Lys |
|---|---|---|---|---|---|---|---|---|---|---|
| 1 | 2.6 | 1.2 | 0.8 | 0.8 | 0.4 | 0.3 | 0.2 | 0.1 | 0.1 | 0.1 |
| 2 | 2.1 | 0.7 | 1.0 | 0.3 | 0.4 | 0.2 | — | 0.2 | — | — |
| 3 | 1.2 | 0.5 | — | 0.2 | 0.3 | 0.3 | — | 0.2 | — | — |
| 4 | 0.5 | 0.3 | — | — | 0.1 | 0.1 | — | 0.1 | — | — |
| 5 | 0.3 | 0.2 | — | — | — | — | — | — | — | — |
| 6 | 0.2 | 0.1 | — | — | — | — | — | — | — | — |
| 7 | 0.1 | 0.1 | — | — | — | — | — | — | — | — |

(≧0.1 n mol)

TABLE 5

Dose Dependency of Glycyl-penta-Glutaminate (GpG) to the Activity for Inhibiting Multiplication of Toxoplasma

| Concentration of GpG (mg/ml) | Percentage of Cells Containing Toxoplasma (%) | | | Toxo-GIF Activity (%) | Cyto-toxicity |
|---|---|---|---|---|---|
| | 0 Tp | 1 to 5 Tp | ≧6 Tp/cell | | |
| 0     | 84.0 ± 1.6  | 26.8 ± 7.1 | 5.0 ± 2.3 | —    | —  |
| 1.000 | 99.8 ± 0.4  | 0.2 ± 0.4  | 0         | 98.8 | ±  |
| 0.500 | 99.4 ± 0.5  | 0.6 ± 0.5  | 0         | 96.3 | —  |
| 0.250 | 93.4 ± 6.3  | 4.2 ± 4.1  | 2.4 ± 2.4 | 58.8 | —  |
| 0.100 | 90.8 ± 6.4  | 5.2 ± 3.4  | 4.0 ± 3.4 | 42.5 | —  |
| 0.050 | 88.4 ± 7.6  | 7.0 ± 4.5  | 4.6 ± 4.2 | 27.5 | —  |
| 0.025 | 82.6 ± 10.8 | 9.8 ± 6.3  | 7.6 ± 4.8 | −8.8 | —  |

(means ± S.D.)

The Toxo-GIF activities of GpG in the canine monocytes and in the human cardiac muscle cell as somatic cells were measured to confirm that appreciable Toxo-GIF activities were found in the cells, as will be apparent from Table 6, so that GpG did not exhibit species specificity similar to the crude Obioactin.

The presence or absence or synergistic effects of the combinations of highest active peptide, GpG, with other synthesized peptides had been also examined. As shown in the following Table 7, no synergistic effect was observed even when 0.5 mg/ml of respective peptides were added to 0.5 mg/ml of GpG.

TABLE 6

Effect for Inhibiting Multiplication of Toxoplasma by Glycyl-penta-glutaminate (GpG) in Heterologous Cells

| Cell | Concentration of GpG (mg/ml) | Percentage of Cells Containing Toxoplasma (%) | | | Toxo-GIF Activity (%) | Cytotoxicity |
|---|---|---|---|---|---|---|
| | | 0 Tp | 1 to 5 Tp | ≧6 Tp/cell | | |
| Mouse Macrophages | 0    | 76.6 ± 9.2  | 16.5 ± 5.1 | 7.2 ± 4.3  | —    | — |
|                   | 0.05 | 88.4 ± 7.6  | 7.0 ± 4.5  | 4.6 ± 4.2  | 50.4 | — |
| Dog Monocytes     | 0    | 40.1 ± 15.5 | 28.5 ± 6.8 | 31.3 ± 8.2 | —    | — |
|                   | 0.05 | 80.5 ± 6.4  | 12.8 ± 5.4 | 6.7 ± 3.3  | 67.4 | — |
| Human Cardiac Muscle | 0 | 54.4 ± 18.3 | 23.5 ± 9.3 | 22.1 ± 9.7 | —    | — |
|                   | 0.05 | 80.7 ± 6.1  | 10.6 ± 3.4 | 8.7 ± 2.1  | 57.7 | — |

(means ± S.D.)

TABLE 7

Synergistic Effect of Synthesized Peptides

| Sample | | Percentage of Cells Containing Toxoplasma (%) | | | Toxo-GIF Activity (%) | Cytotoxicity |
|---|---|---|---|---|---|---|
| A (0.5 mg/ml) | B (0.5 mg/ml) | 0 Tp | 1 to 5 Tp | ≧6 Tp/cell | | |
| Control (Tc-199) | | 76.6 ± 9.2 | 16.2 ± 5.1 | 7.2 ± 4.3 | — | — |
| GpG | GpG | 100        | 0         | 0         | 100  | ++ |
| GpG | —   | 100        | 0         | 0         | 100  | —  |
| GpG | pA  | 95.6 ± 2.3 | 4.0 ± 1.9 | 0.4 ± 0.5 | 81.2 | +  |
| GpG | pG  | 98.0 ± 1.0 | 2.0 ± 1.0 | 0         | 91.5 | ±  |
| GpG | GpA | 91.4 ± 4.7 | 7.8 ± 4.8 | 0.8 ± 0.4 | 63.2 | ±  |
| GpG | ApA | 91.4 ± 5.7 | 8.6 ± 5.2 | 0.2 ± 0.4 | 61.5 | —  |
| GpG | ApG | 100        | 0         | 0         | 100  | ++ |

(means ± S.D.)

As has been described hereinbefore, we have investigated to refine Obioactin which is an immunoreglator for enhancing physiological cell functions and to identify the sequence of amino acids in the Obioactin. Our investigations have revealed that the oligopeptide GpG is the active unit or core of Obioactin. We have further investigated to confirm the Toxo-GIF activity of GpG which has an activity 10 to 20 times as high as that of crude obioactin on weight basis and even 40 to 140 times as high as that of the latter on mole basis. GpG exhibits no species specificity, similar to crude Obioactin, and thus this peptide as an immunoregulator is applied for various animals and human being in an immunodeficiency status.

List of Reference Documents

1. Sethi, K. K. et al., J. Immunol., 131, pp 1151 to 1558 (1975)
2. Shirahata, T., Shimizu, K. & Suzuki, N., Z. Parasitenkd., 49, pp 11 to 23 (1976)
3. Nagasawa, H. et al., Immunobiol., 156, pp 307 to 319 (1980)
4. Matsumoto, Y. et al., Zbl. Bakt. Hyg. A., 250, pp 383 to 391 (1981)
5. Unexamined Japanese Patent Publication No. 142922/1982
6. Unexamined Japanese Patent Publication No. 144983/1982
7. U.S. Pat. No. 4,482,543
8. Suzuki, N. et al., Zbl. Bakt. Hyg. I. Abt. Orig. A., 250, pp 356 to 366 (1984)
9. Suzuki, N. et al., Zbl. Bakt. Hyg. I. Abt. Orig. A., 256, pp 367 to 380 (1984)
10. Igarashi, I. et al., Zbl. Bakt. Hyg. I. Abt. Orig. A., 244, pp 472 to 482 (1979)
11. Nagasawa, H. et al., Jpn. J. Vet. Sci., 43, pp 307 to 319 (1981)

12. Sakurai, H., et al., Jpn. J. Trop. Med. Hyg., 10, pp 183 to 195 (1982)

13. Benson R. J. et al., Proc. Nat. Acad. Sci., USA, 72, pp 619 to 622 (1975)

14. Bohlen, P., "Method in Enzymology", 91, pp 17 to 26 (1983)

15. Kent, S. B., et al., "Peptides 1984", edited by U. Ragnarsen,(Almqvist and Wiksell, Stockholm, Sweden, 1984), p185

16. Kent, S. B. H., et al., "Peptide Chemistry", edited by N. Izumiya, (Protein Research Foundation, B. H. Osaka, Japan, 1985L ), p 217

17. Osaki, H. et al., Zbl. Bakt. Hyg. I. Abt. Orig. A., 256, pp 328 to 334 (1984)

What is claimed is:

1. A biologically active peptide having an activity to inhibit Toxoplasma multiplication and composed of an amino acid sequence of the formula:

Gly-Glu-Glu-Glu-Glu-Glu.

2. A biologically active peptide having an activity to inhibit Toxoplasma multiplication and composed of an amino acid sequence of the formula:

Glu-Glu-Glu-Glu-Glu.

3. A biologically active peptide having an activity to inhibit Toxoplasma multiplication and composed of an amino acid sequence of the formula:

Asp-Asp-Asp-Asp-Asp.

4. A biologically active peptide having an activity to inhibit Toxoplasma multiplication and composed of an amino acid sequence of the formula:

Ala-Asp-Asp-Asp-Asp-Asp.

* * * * *